United States Patent [19]

Jolly

[11] Patent Number: 5,186,842
[45] Date of Patent: Feb. 16, 1993

[54] METHOD FOR REMOVING LOW MOLECULAR WEIGHT CONTAMINANTS

[75] Inventor: Clifford D. Jolly, Roseburg, Oreg.

[73] Assignee: Umpqua Research Company, Myrtle Creek, Oreg.

[21] Appl. No.: 730,216

[22] Filed: Jul. 15, 1991

[51] Int. Cl.$^5$ ............ C02F 1/72; C12N 9/02; C12N 11/14

[52] U.S. Cl. .............. 210/763; 210/500.32; 210/632; 210/660; 210/908; 435/25; 435/140; 435/141; 435/147; 435/176; 435/189; 435/262; 435/264

[58] Field of Search ........... 210/259, 632, 763, 908, 210/660, 762, 669, 500.23, 321.6, 497.1; 204/403; 435/136, 140, 141, 176, 180, 262, 264, 25, 189, 147, 288; 502/331

[56] References Cited

U.S. PATENT DOCUMENTS

| | | | |
|---|---|---|---|
| 3,344,037 | 9/1967 | Leavitt | 435/136 |
| 4,115,264 | 9/1978 | McCarthy et al. | 210/762 |
| 4,485,016 | 11/1984 | Hopkins | 210/632 |
| 4,863,608 | 9/1989 | Kawai et al. | 210/763 |
| 4,871,669 | 10/1989 | Murray et al. | 435/147 |
| 4,877,558 | 10/1989 | Morioka et al. | 210/763 |
| 4,920,055 | 4/1990 | Holberg et al. | 435/147 |
| 5,010,005 | 4/1991 | Duff et al. | 435/180 |
| 5,037,610 | 8/1991 | Fukasawa et al. | 210/500.23 |
| 5,057,421 | 10/1991 | Hofmann et al. | 210/632 |

Primary Examiner—Robert A. Dawson
Assistant Examiner—Sun Uk Kim
Attorney, Agent, or Firm—Marger, Johnson, McCollom & Stolowitz

[57] ABSTRACT

A method of the present invention is provided for removing low molecular weight contaminants from a contaminant-containing material. This contaminant-containing material can include alcohol compounds, aldehyde compounds and peroxide compounds. The method comprises providing an alcohol oxidase enzyme-based catalyst system including coimmobilized transition metals comprising platinum and copper for catalytically oxidizing the contaminant-containing material. Then, the contaminant-containing material is catalytically oxidized in the presence of the alcohol oxidase enzyme-based catalyst system to form organic acid compounds. The organic acid compounds can then be removed.

21 Claims, 14 Drawing Sheets

| SUB-BED | QTY. |
|---|---|
| MCVRT | 60cc |
| IRN-150 | 60cc |
| IRA-60 | 350cc |
| Pt/C CATALYST | 360cc |
| ALCOHOL OXIDASE | 200cc |
| IRN-150 | 60cc |
| | 1090cc |

METHOD FOR REMOVING LOW MOLECULAR WEIGHT CONTAMINANTS

BACKGROUND OF THE INVENTION

Previous work in this area provided a proof-of-concept for the utilization of immobilized enzyme beds as biocatalytic reactors. see Jolly, C. D. and Bagdigian, R. M., "Application of Biocatalysts to Space Station ECLSS and PMMS Water Reclamation" SAE Technical Series 891442; and Putnam, D. F., et al, "Space Station Hygiene Water Reclamation by Multifiltration", presented at the 21st ICES, July 1991. A 7 cc urease bed was demonstrated to be capable of removing 30 mg/L urea for a volume of 35 liters, a throughput of 5 L/cc media. The material also integrated with multifiltration media to remove all measurable urea from waste shower water. An alcohol oxidase bed was demonstrated to be effective for only 800 mL throughput of a solution containing 50 ppm(v/v) methanol. It was determined that the enzyme was rapidly denatured by the hydrogen peroxide produced in the enzymatic reaction. It was concluded that a means of decomposing the $H_2O_2$ in situ was required if reasonable bed life was to be attained. Several methods were defined at that time.

SUMMARY OF THE INVENTION

Removal of low-molecular weight, polar, non-ionic contaminants such as urea and alcohols from aqueous solution is being accomplished by this invention by using immobilized enzyme technology. Immobilized urease is used to catalyze urea hydrolysis for subsequent removal as ammonia. An alcohol oxidase enzyme-based catalyst system including co-immobilized transition metals comprising platinum and copper is used to catalyze oxidation of alcohols, aldehydes, and similar compounds to organic acids, which are removed by ion exchange.

Fixed bed reactors were successfully developed and delivered to NASA-MSFC for a segment of the Phase III Core Module Integrated Facility (CMIF) Water Recovery Test. Wastewater generated in the End-use Equipment Facility (EEF) was purified using a combination of Multifiltration Unibeds and Enzyme Unibeds. The enzyme beds effectively removed the targeted organics to levels below detection limits (<100–400 ppb). Also, based on the amount of TOC removed, the enzyme beds removed unidentified organic contaminants beyond those specifically targeted. Average effluent TOC concentrations were 1 mg/L.

Technologies to optimize efficiency of water reclamation systems on Space Station Freedom (SSF) and advanced missions are currently being developed. Multifiltration (MF), including fixed sorbent beds (unibeds) is the baseline technology for the removal of contaminants from SSF wastewater. The adsorption and ion-exchange technologies used in the MF system have proven to be highly efficient at removing most of the contaminant load encountered in all tests to date. Low molecular weight, polar, non-ionic compounds such as alcohols and urea are not well removed, however. Immobilized enzyme catalysts have been developed to catalyze oxidation and decomposition reactions to allow more efficient removal of these compounds from Process Material Management System (PMMS) and Environmental Control and Life Support System (ECLSS) wastewater.

The immobilized enzyme catalysts are prepared by binding the enzyme to a derivatized support, usually silica-based materials. The catalyst is heterogenous, which allows operation as a fixed bed, preventing secondary contamination of the waste stream that it is used to purify. The immobilization process also confers three-dimensional stability, which allows a wider variation of conditions (i.e. pH, temperature, conductivity) under which the enzyme can operate without being denatured, compared to a free enzyme in solution. In addition, these bound enzymes are in a form that is convenient to use as a component sub-bed in a multifiltration unibed. There is a very low specific energy demand, requiring only that the water stream be pumped through the bed. The enzymes are highly efficient, able to catalytically convert large amounts of contaminants. The materials are also durable, having been tested to over 600 liters throughput without any measurable mechanical or physical breakdown of the media. Extensive total organic carbon, conductivity, and specific contaminant analyses of column effluents have shown that no significant secondary contamination can be attributed to the biocatalysts.

Urea and alcohols are major components of current waste streams that are not well removed by conventional phase change, multifiltration, and reverse osmosis (RO) contaminant removal techniques. Two different enzyme unibed reactors have been designed to remove these contaminants. The urease enzyme bed effects the hydrolysis of urea to ammonia as described by Equation 1, as follows:

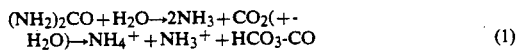

The products, ammonium and bicarbonate ions are both readily removed by ion exchange resins.

Primary alcohols as well as a number of other compounds are oxidized to their corresponding aldehydes by the alcohol oxidase enzyme bed. These aldehyde products then undergo a facile oxidation to organic acids using a low-temperature heterogenous supported metal catalyst. Equation 2 and 3 describe the general chemical reactions for this process, as follows:

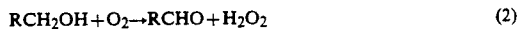

The organic acids are then efficiently removed by ion-exchange.

The hydrogen peroxide produced by the enzymatic reaction is an inhibitor to the progress of the reaction. An in situ method has been developed to reduce the peroxide thereby providing significantly longer enzyme bed life, making the material suitable for process applications. The alcohol oxidase reactor uses molecular oxygen, $O_2$, as the oxidant in stoichiometric quantities. Introduction of oxygen into the system is accomplished using an oxygen saturator developed in-house. The saturator is a hollow fiber, non-porous membrane bundle available in polycarbonate or stainless steel housings. The configuration used for this program is diagrammed in FIG. 1. This device provides excellent distribution of dissolved oxygen in a process stream. It also avoids two-phase flow that would occur if $O_2$ were simply injected into the closed system, which could

3 lead to gas bubble entrapment in the downstream media, resulting in bed channeling or flow restriction.

DETAILED DESCRIPTION OF A PREFERRED EMBODIMENT

Test Methods & Results

Figure 1:
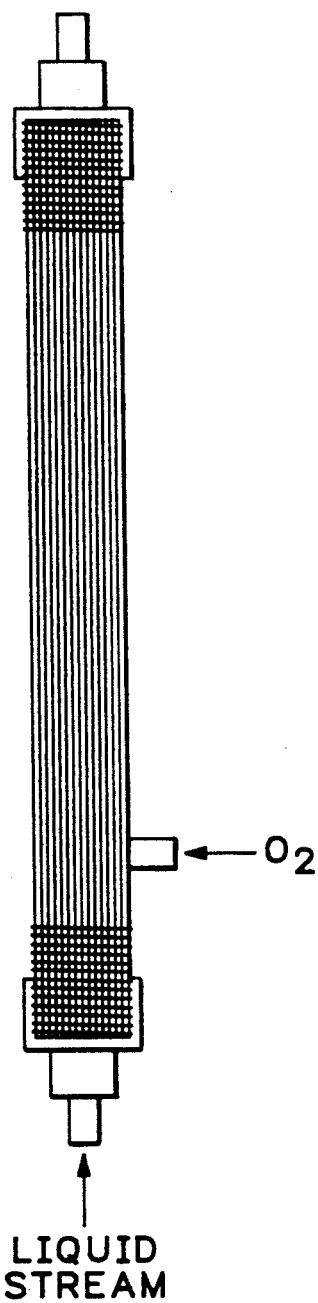
FIG. 1 is a pictorial representation of the oxygen saturator of the present invention.
Figure 2:
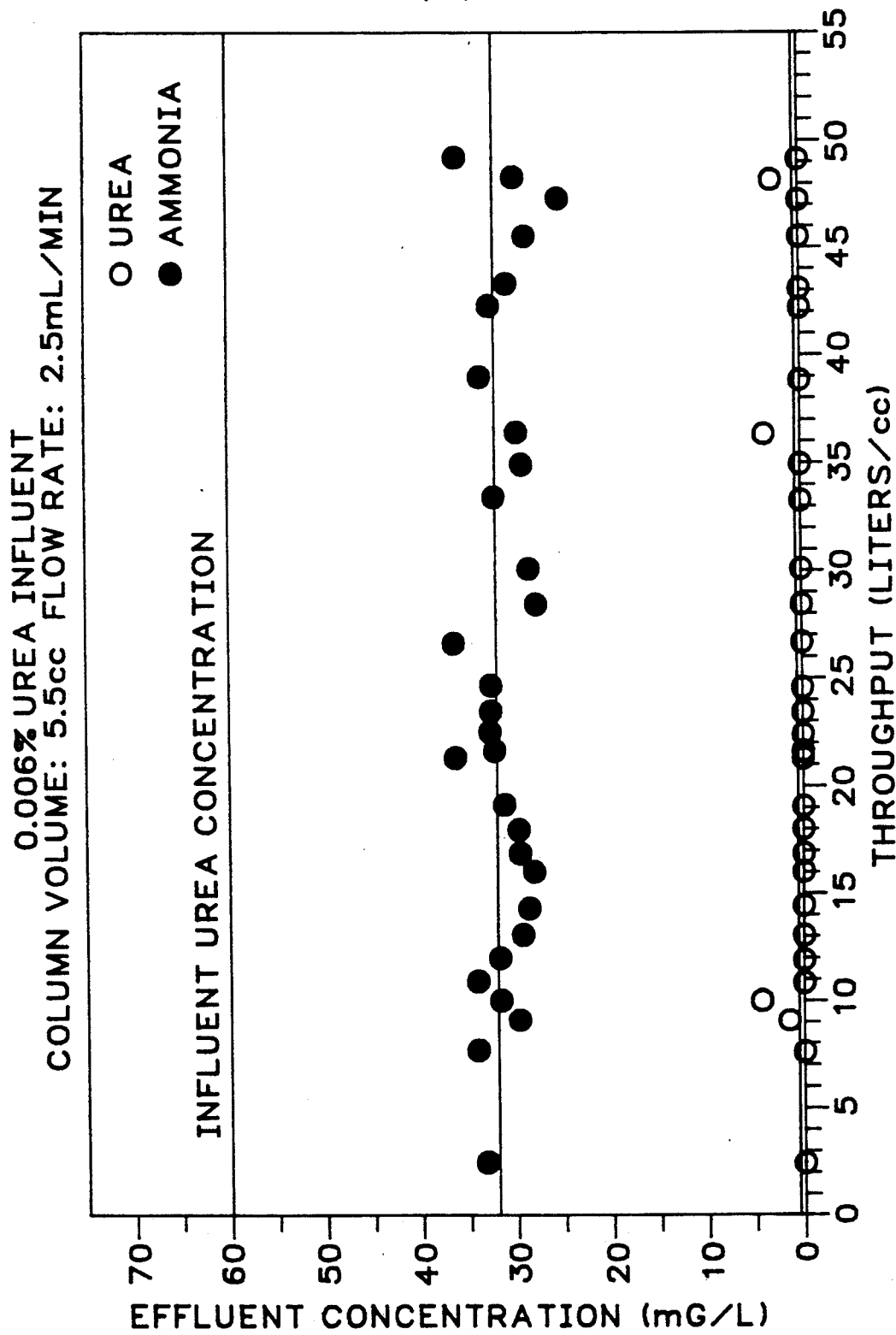
FIG. 2 is a graphical representation of effluent concentration v. throughput for a Urease Test Column at 0.006% urea influent.
Figure 3:
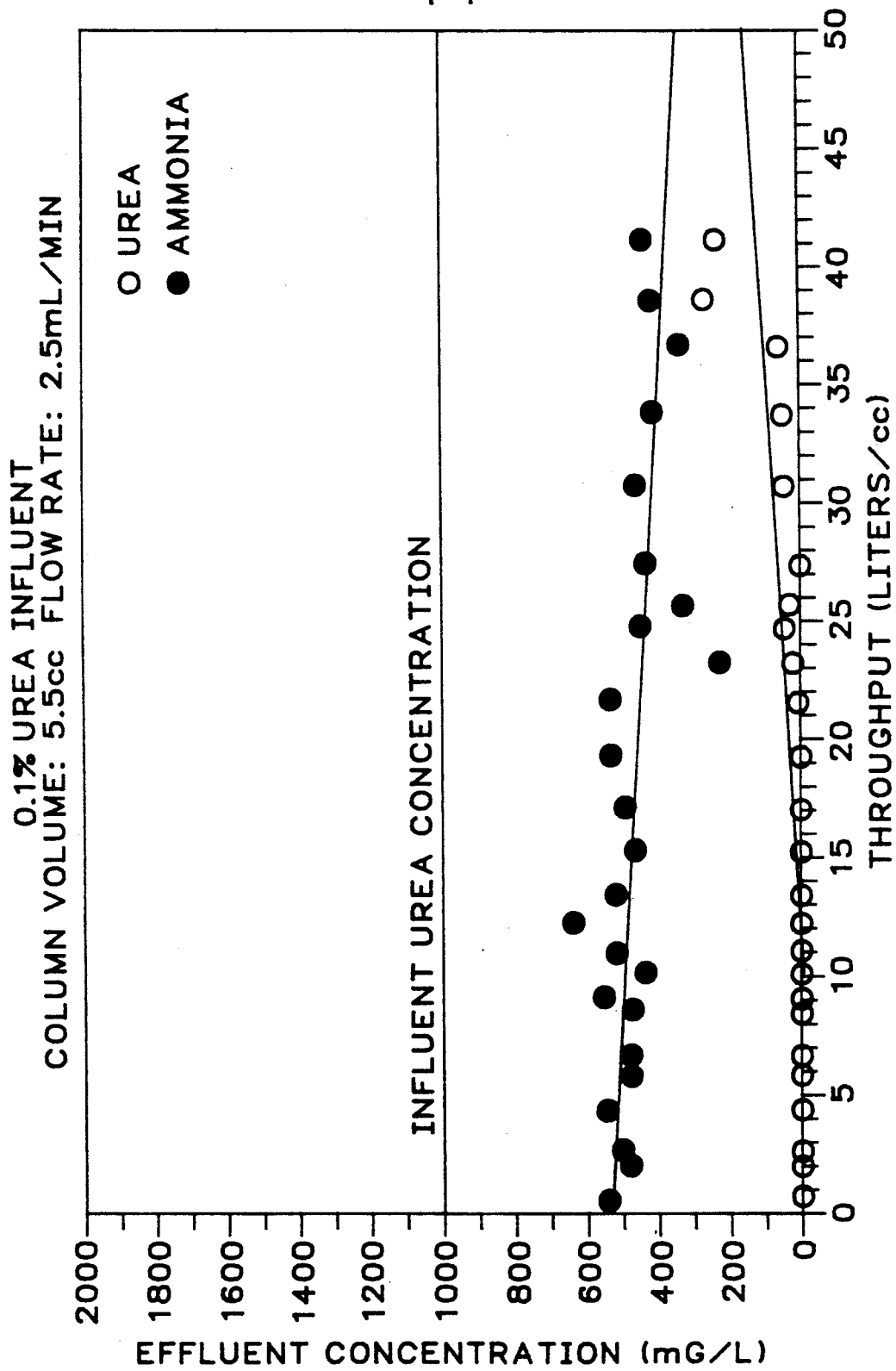
FIG. 3 is a graphical representation of effluent concentration v. throughput for a Urease Test Column at 0.1% urea influent.
Figure 4:
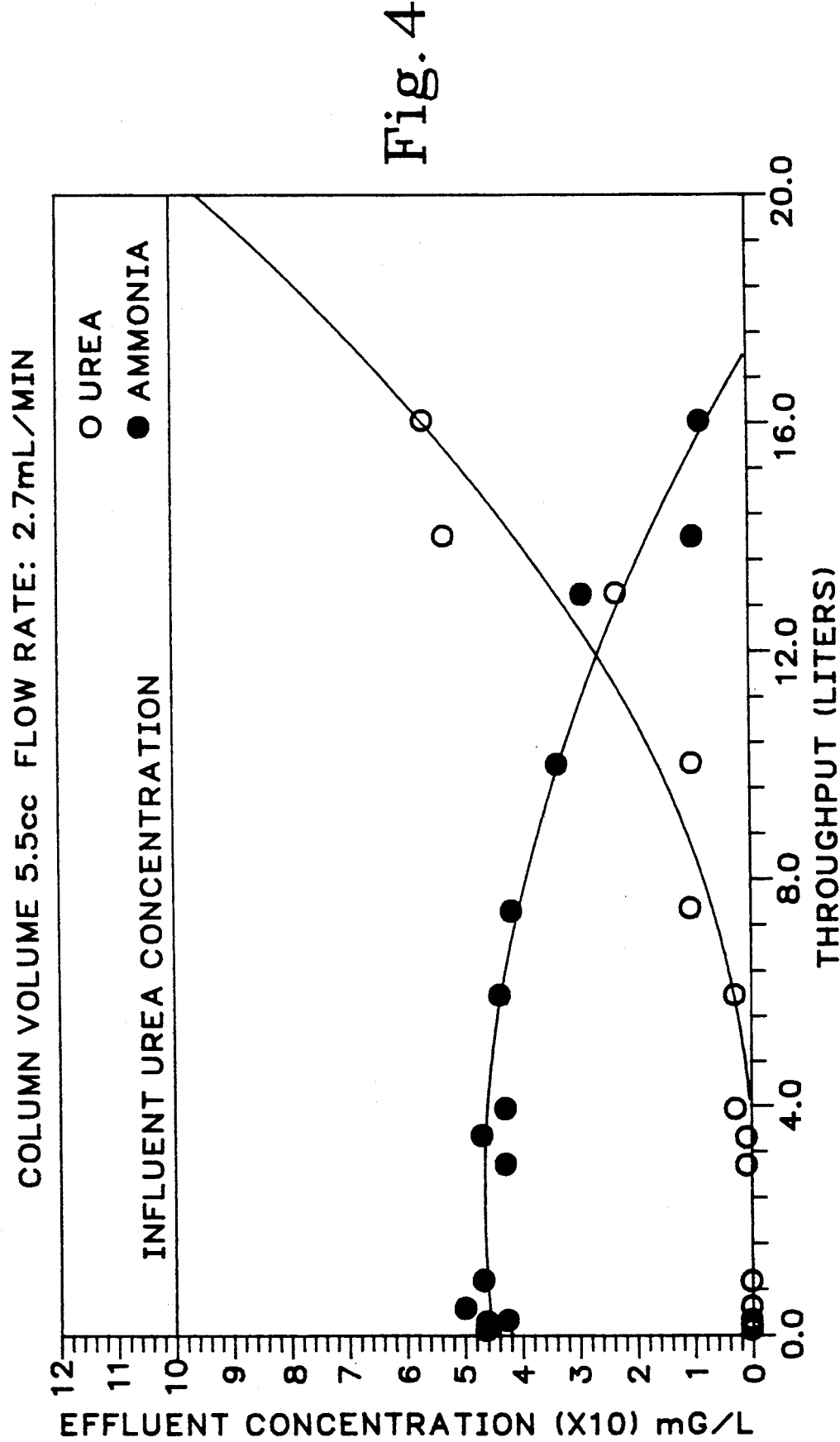
FIG. 4 is a graphical representation of effluent concentration v. throughput for a Urease Test Column at 1% urea influent.

Five $cm^3$ immobilized urease columns are now capable of completely removing 60 mg/L urea from a water stream for over six months and 270 liters throughput. Data are shown in FIG. 2. This test column converted all of the urea to ammonia. There was no measured loss of activity under these conditions during five months of continuous operation. Similar columns have been challenged with higher concentrations of urea, to determine the limit of the initial activity of the enzyme bed. These data are shown in FIGS. 3 and 4.

Figure 5:
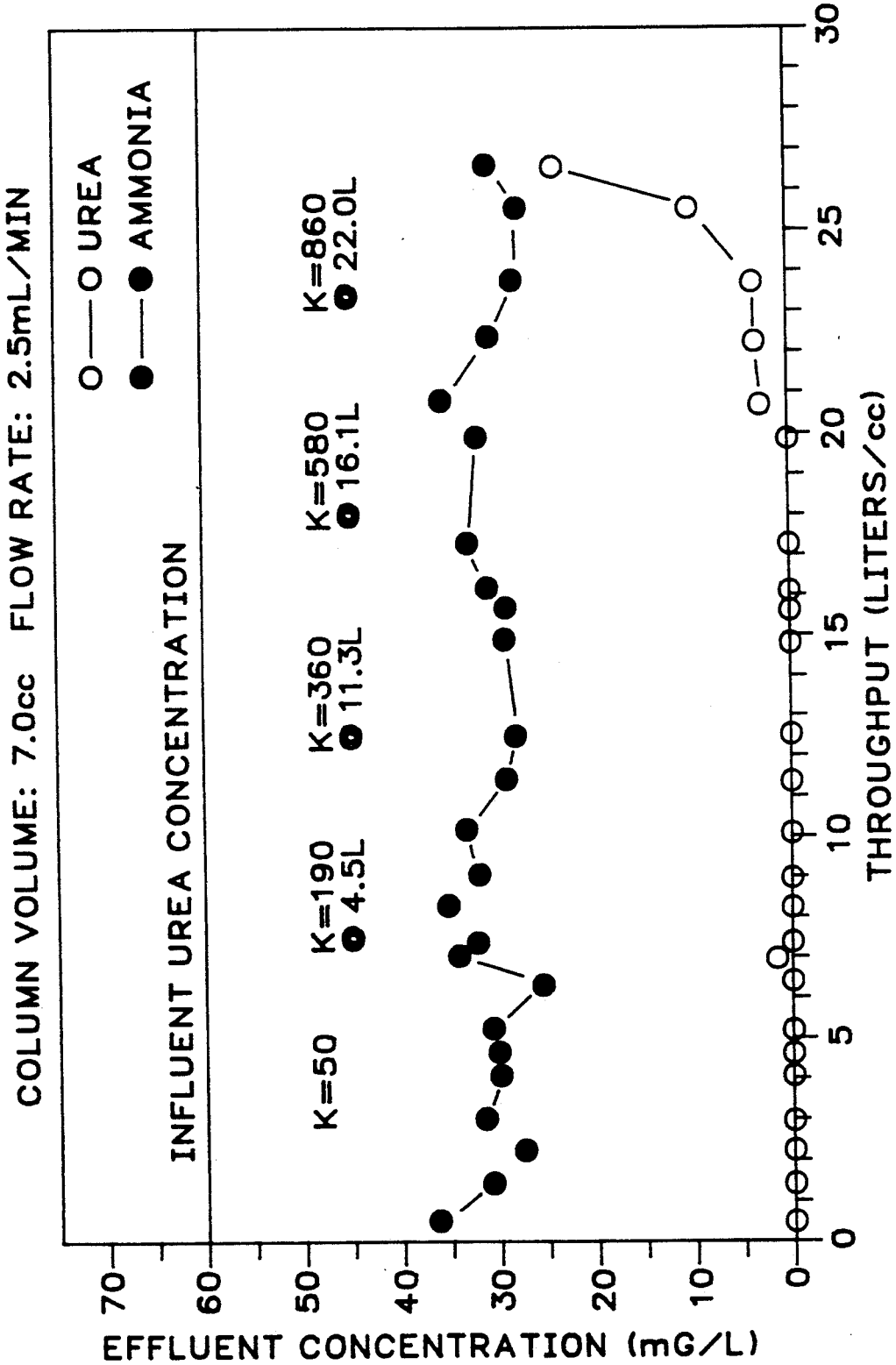
FIG. 5 is a graphical representation of effluent concentration v. throughput for a Urease Conductivity Test Column.
Figure 6:
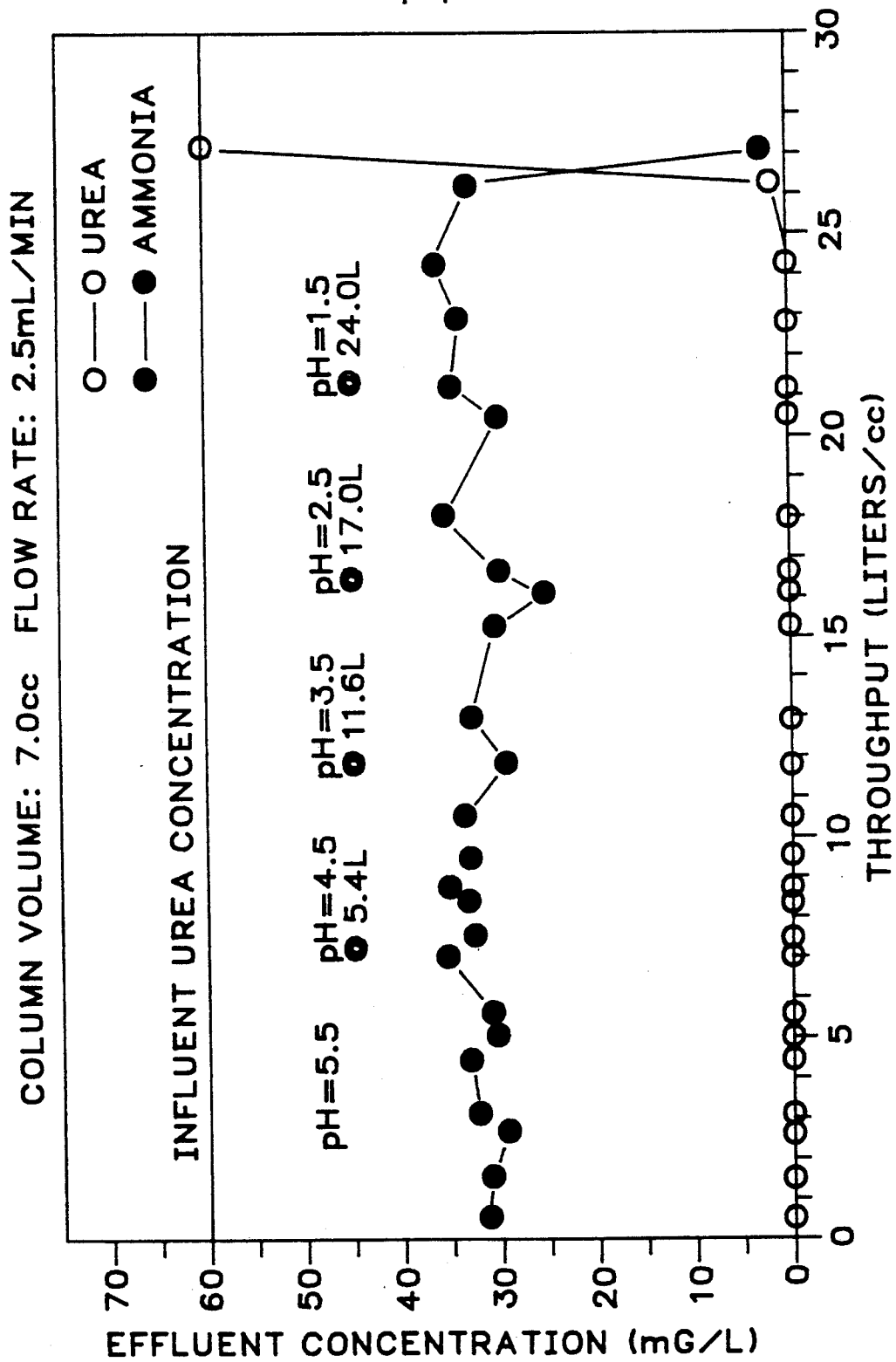
FIG. 6 is a graphical representation of effluent concentration v. throughput for a Urease pH Test Column.

A pair of 7 cc urease columns prepared from the same batch of material were challenged with increasing conductivity and decreasing pH respectively (FIGS. 5 & 6). Each influent contained 60 mg/L urea and had either NaCl or HCl added to modify the column conditions. The columns were run for 5 L/cc before each change occurred. The data show that increasing the conductivity up to K=580 micromho/cm did not hinder the performance of the bed. In the pH test, there was no loss of activity for the enzyme at pH=5.5, 4.5, or 3.5, or 2.5 through a total volume of 20 L/cc.

Additional standardized parametric tests using a challenge stream iodinated by a microbial check valve (MCV) indicate that $I_2$ (1-2 mg/l) significantly decreases the activity of the enzyme. Use of mixed bed ion-exchange resin upstream of the biocatalyst protects the enzyme from denaturation by $I_2$ or any heavy metals in the waste stream.

Figure 7:
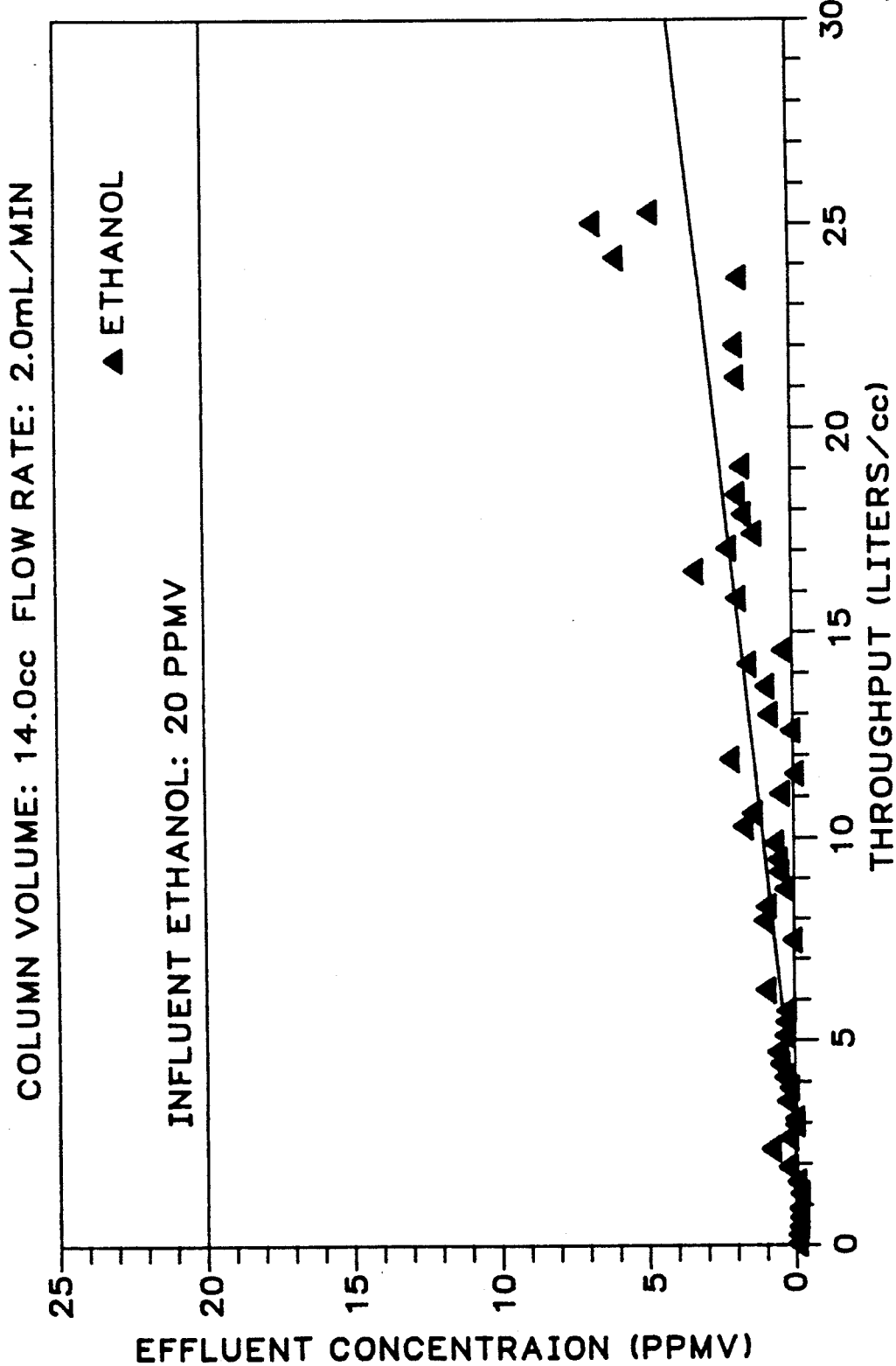
FIG. 7 is a graphical representation of effluent concentration v. throughput for an Alcohol Oxidase Test Column.
Figure 8:
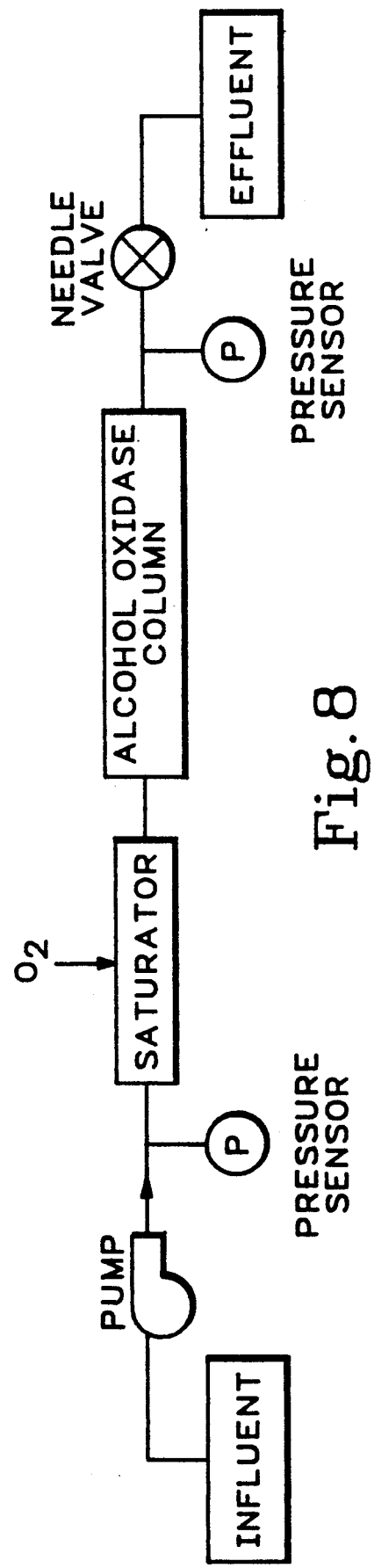
FIG. 8 is a schematic flow diagram of a pressurized alcohol oxidase fixed bed reactor system.

The current state-of-the-art alcohol oxidase column is capable of removing 20 ppm(v/v) ethanol from solution for nearly 20 L/cc (FIG. 7). This material removes over 95% of the alcohol in the challenge stream through the first 10 L/cc and continues at about 90% removal through the second 10 L/cc. This material is used in conjunction with a supported platinum catalyst designed to promote conversion of aldehydes to organic acids. This is advantageous in that organic acids are more efficiently removed by ion-exchange media than aldehydes, and are much less toxic. The concentration of ethanol that can be oxidized is limited by the stoichiometric requirement for oxygen dissolved in the influent solution. Increasing the system pressure allows a higher dissolved $O_2$ concentration, in accordance with Henry's Law. A high-pressure reactor that is capable of oxidizing much higher concentrations of alcohol was constructed and tested. The design is shown in FIG. 8. An oxygen saturator was used to provide $O_2$ to the pressurized system.

Figure 9:
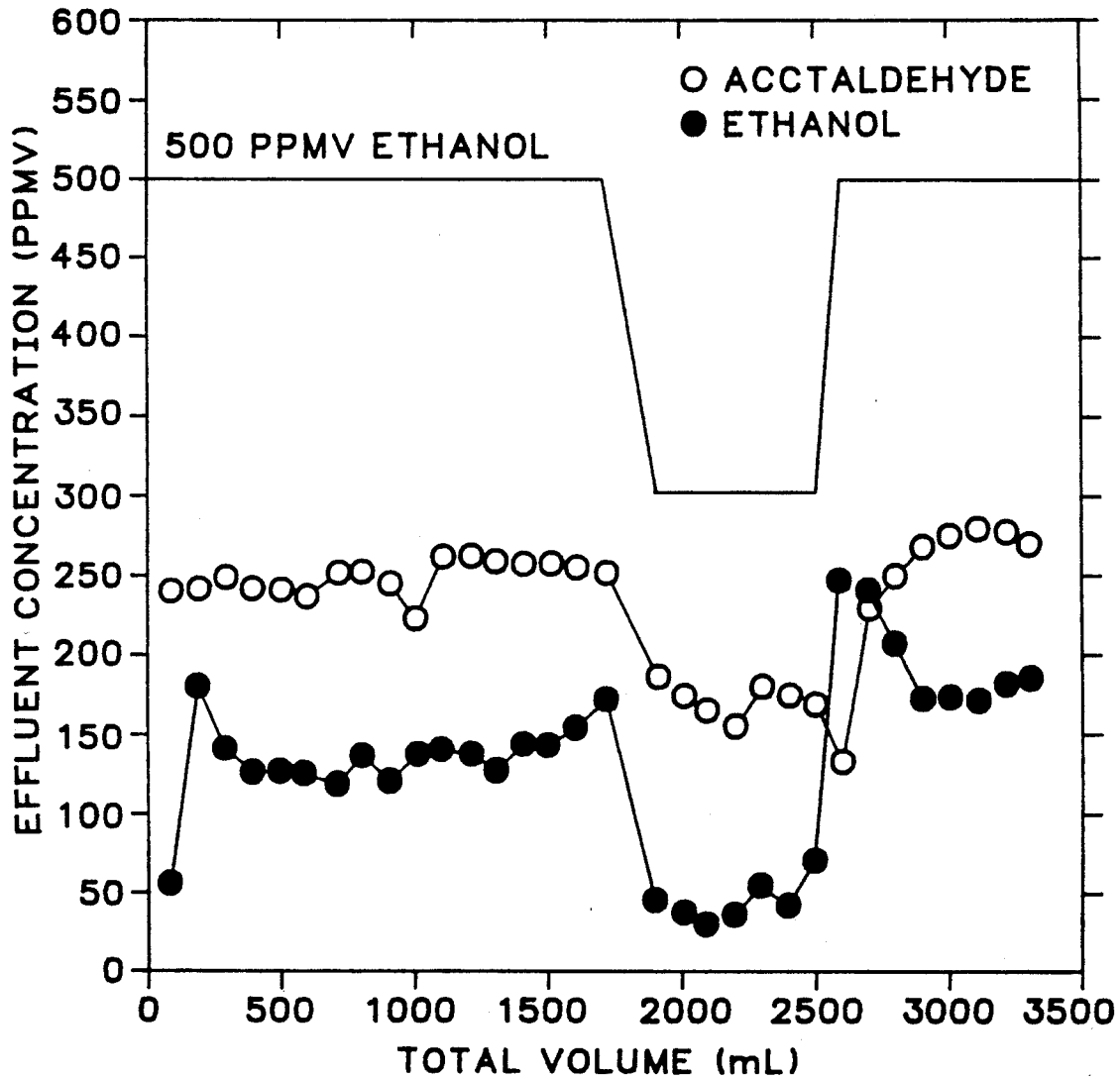
FIGS. 9 and 10 are graphical representations of effluent concentration v. total volume for a Hi-Pressure Alcohol Oxidase Reactor.
Figure 10:
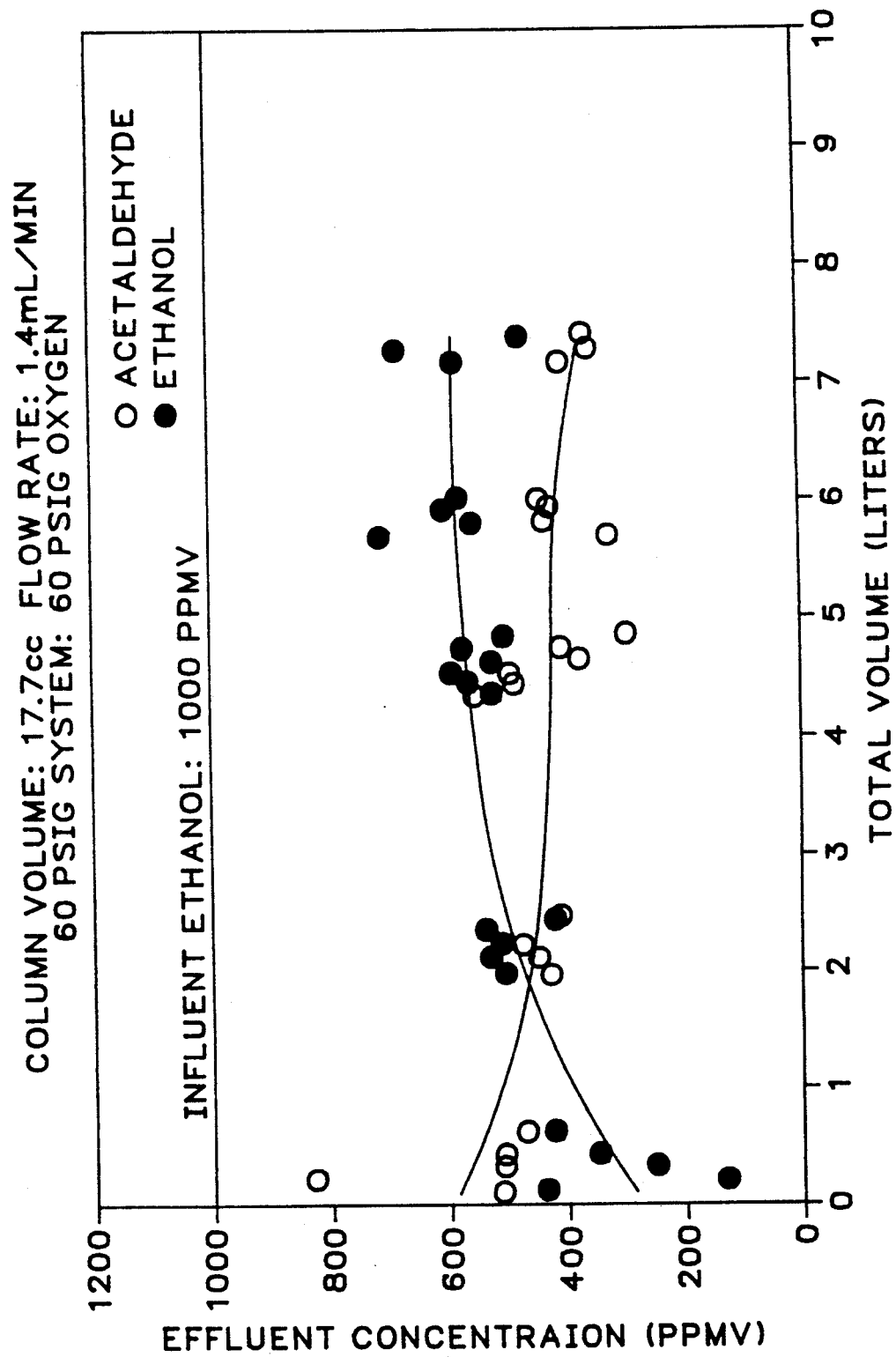

The initial test of the high-pressure reactor involved running four liters of 500 ppm(v/v) ethanol through a 14.0 cc alcohol oxidase bed at 40 psig system pressure and 30 psig oxygen pressure, at a flow rate of 2.0 mL/min. During the test, 300 ppm(v/v) ethanol was substituted as the influent for 0.5 liters, then 500 ppm(v/v) was restored (FIG. 9). The column consistently oxidized 50% of the ethanol at the higher concentration and 60% at the lower level. The previous performance level was observed after the return to 500 ppm(v/v). Additionally, a column containing 17.7 cc media was challenged at 60 psig with 1000 ppm(v/v) ethanol at a 1.4 mL/min flow rate, 40% of the ethanol was oxidized for a duration of seven liters of influent (FIG. 10). In all cases, the oxidation was limited by the $O_2$ concentration.

Design of Fixed Bed Reactors

Two prototype biocatalytic reactors were designed, fabricated, and delivered to the NASA Marshall Space Flight Center. One reactor is designed for removal of urea and ammonia, and one reactor is designed for removal of alcohols and the other compounds listed in Table 1. Each reactor is a fixed bed consisting of a single 5 cm×60 cm long polycarbonate or stainless steel housing containing 1100 cc of media. The reactors are designed to run at room temperature at a flow rate of 25 mL/min. The reactor beds are composed of several sub-beds containing a minimum volume of 60 cc media to provide a minimum bed length to diameter ratio. The reactors include a sub-bed dedicated to the removal of iodine from the influent solution, and an MCV resin bed on the effluent end to impart an iodine residual to the effluent water for microbial control. The beds were not sterilized prior to shipment. In both designs the bed life is limited by the volume of sorbent material rather than by the immobilized enzyme sub-beds.

Figure 11:
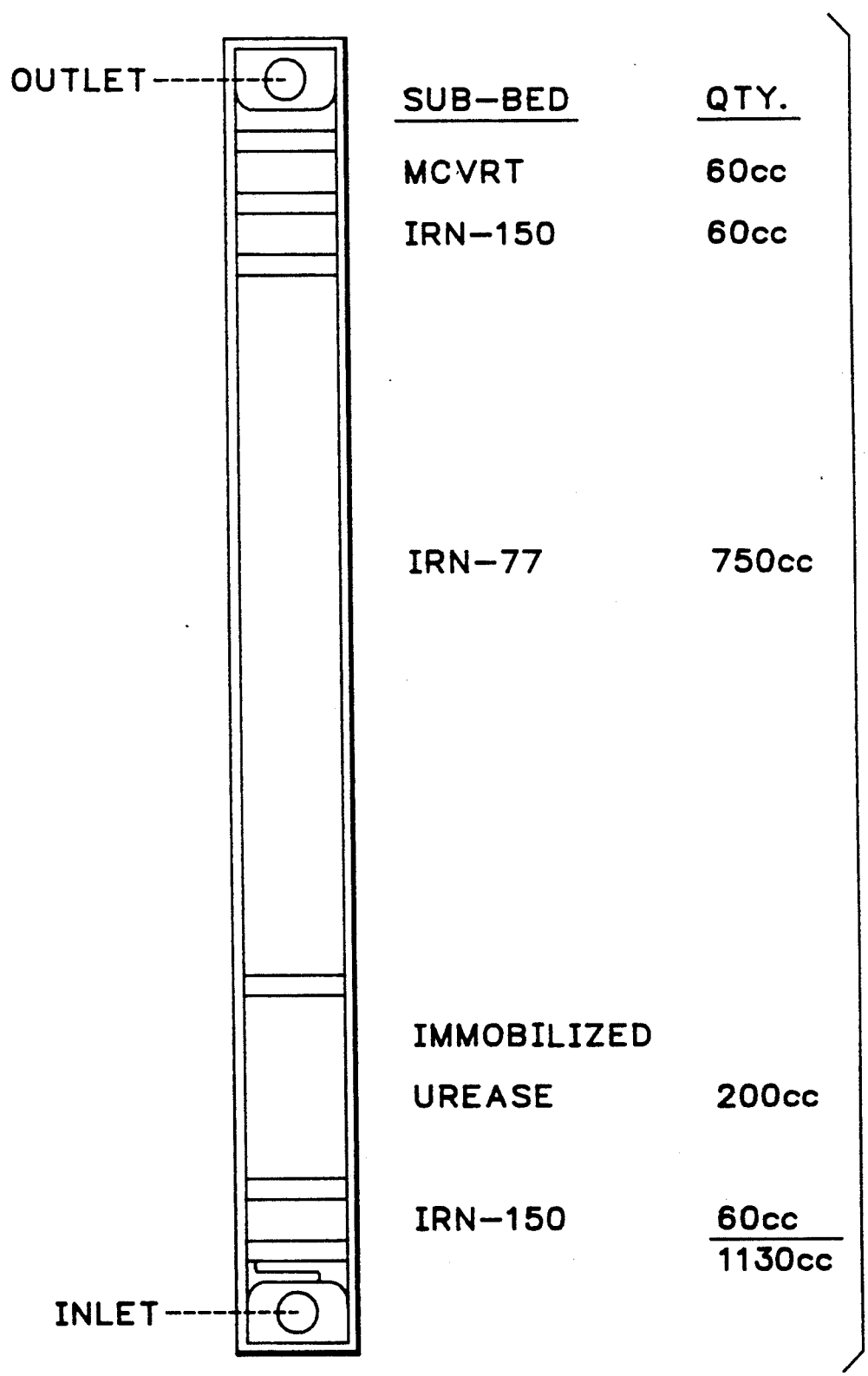
FIG. 11 is a pictorial representation of a Urease Reactor.
Figure 12:
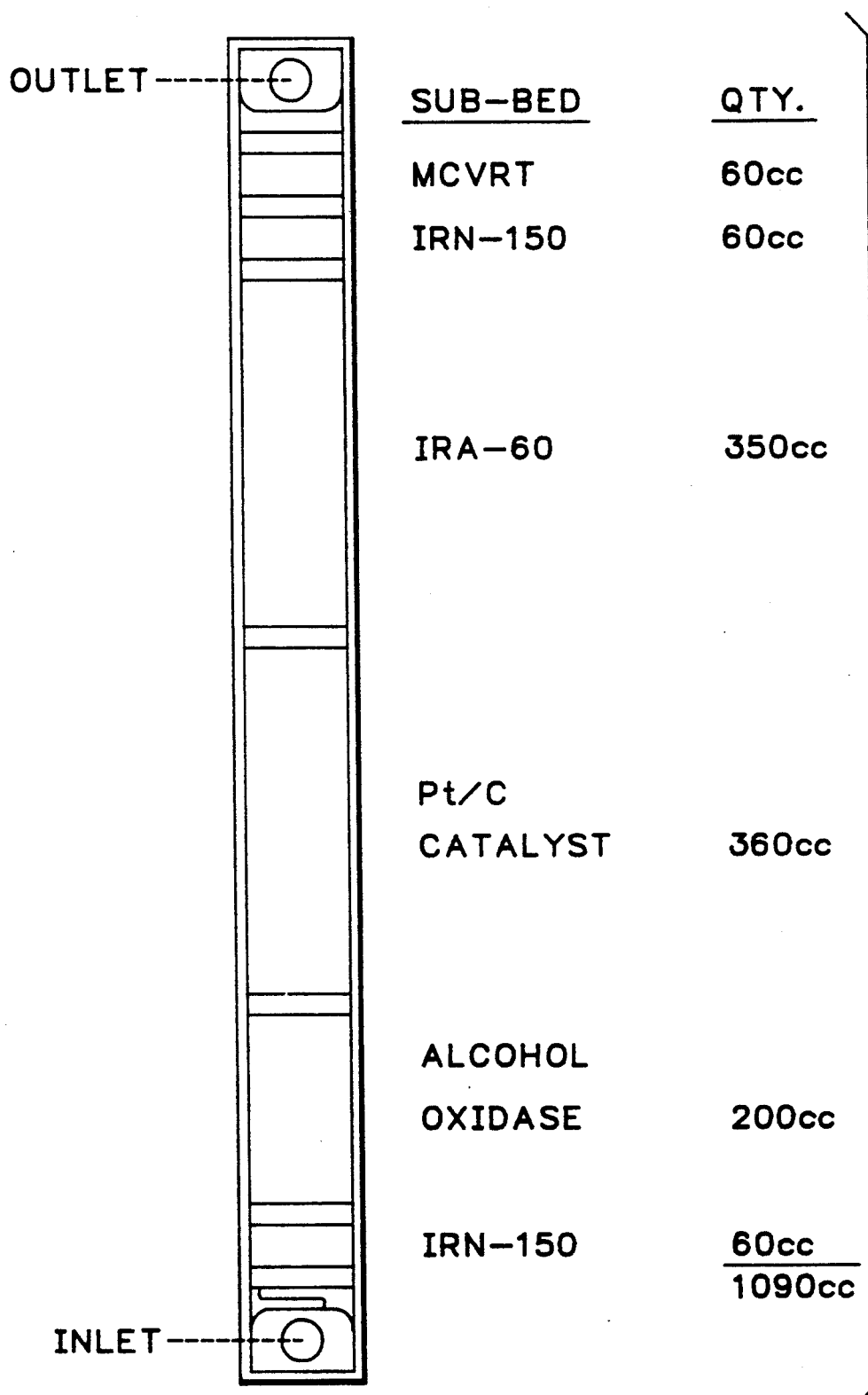
FIG. 12 is a pictorial representation of an Alcohol Oxidase Reactor.

The reactor designs are shown in FIGS. 11 and 12. The urease reactor converts urea to ammonia, then removes the ammonia using cation exchange resin. The alcohol oxidase reactor converts the target compounds to organic acids using both the supported enzyme and a heterogeneous transition metal catalyst. Oxygen is fed into the water stream prior to this unibed by means of an oxygen saturator developed for this and similar applications.

Core Module Integrated Facility Test

Figure 13:
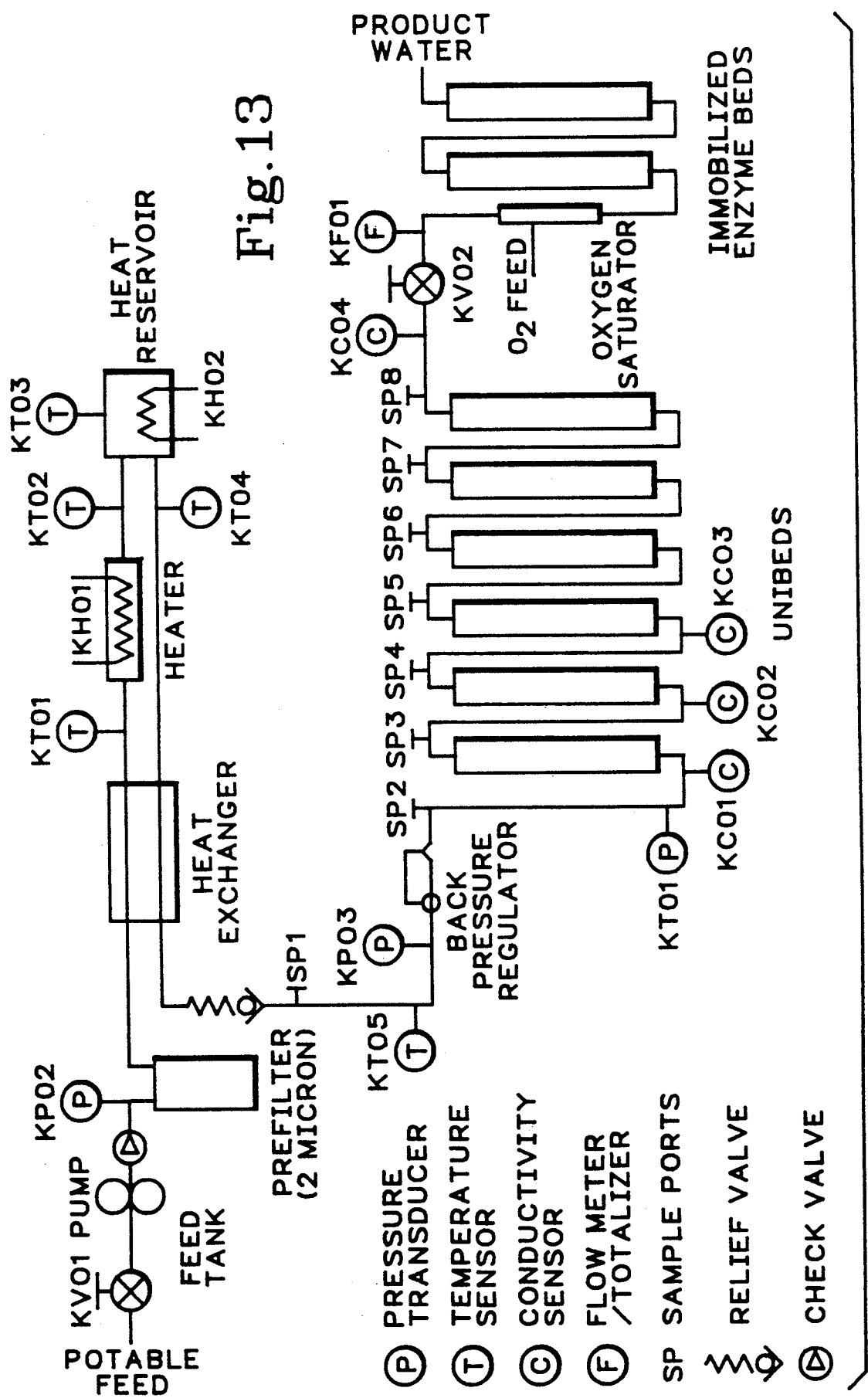
FIG. 13 is a schematic flow diagram of a CMIF MF System.
Figures 14, 15:
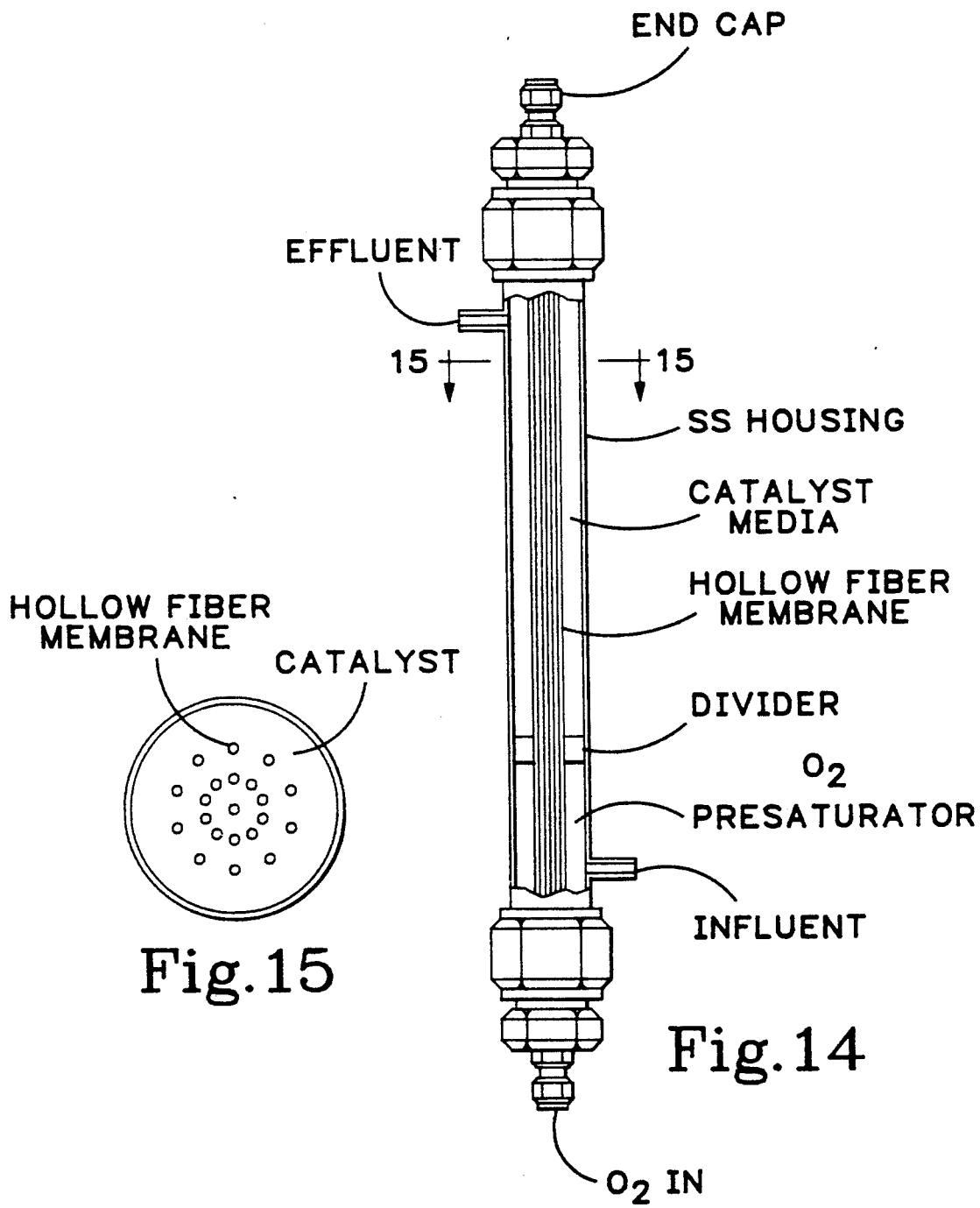
FIG. 14 is a schematic flow diagram of an Alcohol Oxidase/Oxygen Saturator Reactor.

Potable testing of the multifiltration/immobilized enzyme technology took place from Feb. 19, 1991 to Mar. 1, 1991 as part of the ongoing Phase III CMIF Water Recovery Test at the NASA Marshall Space Flight Center. This CMIF test bed was assembled to evaluate the performance of various water reclamation technologies on simulated Space Station Freedom waste waters. The various waste streams are generated in the Enduse Equipment Facility (EEF), a clean room that houses the equipment needed to provide the simulated waste waters. The equipment includes a shower, laundry, microwave, urine collection device, and exercise equipment. Makeup air provided to the EEF is missile grade air, which has a near zero level of humidity, particulates, and organic constituents. The missile grade air is fed to the EEF at a rate that will maintain a carbon dioxide level in the EEF below 1.0% and prevent any leakage into the EEF from the outside. This condition ensures that the condensate collected in the EEF is all metabolic or hygiene condensate, with no contamination from the EEF surroundings. The major components of the multifiltration subsystem are the sterilization assembly and unibed train (see FIG. 13). The immobilized enzyme beds were added as a post-treatment to the unibed train for this test. The feed supplied by the EEF is pumped from the feed tank using a gear pump located at the subsystem inlet. The feed stream passes through a 2.0 micron prefilter and the sterilization assembly, where the sterilizer reservoir maintains a temperature of 121° C. for twenty minutes, thus achieving sterilization conditions. A subsystem pressure of 30 psig is maintained in the sterilizer to prevent flashing. The unibed train consists of six identical unibeds in series. Further information on unibeds and their design is available in Reference 2. An oxygen saturator was installed downstream of the unibeds to provide the excess oxygen needed to oxidize the organics in the enzyme beds. Oxygen was provided at a flow rate of 2 cc/min and 28 psig to the saturator. The two immobilized enzyme beds followed the saturator. The first bed contained the alcohol oxidase enzyme, the second contained the urease enzyme.

A summary of the test results is included in Table 2. The average TOC entering the enzyme beds was 5.3 mg/liter. An average of 1.6 mg/liter of the TOC can be accounted for in the alcohols and urea, leaving 3.7 mg/liter of the TOC entering the enzyme beds uncharacterized. After the immobilized enzyme beds, the average TOC was 1.02 mg/liter (assuming TOC on days 7 and 9 to be 1.0 mg/liter), a decrease of 4.3 mg/liter, or 81% removal of the TOC entering the enzyme beds. Except for methanol on day 2 (0.98 mg/liter), all targeted compounds were reduced to levels below their detection limit on each day. The TOC removed by the oxidation of the targeted compounds is between 1.3 and 1.6 mg/liter, depending upon how far below their detection limit each compound was removed. Accordingly, the targeted compounds make up less than 40% of the TOC removed, which indicates that the immobilized enzyme beds are removing additional organic contaminants. A possible group that would pass through the unibeds and be oxidized in the enzyme beds is glycols. Preliminary lab results indicate their presence in the unibed product water at levels ranging from 3 to 8 ppm. Their subsequent removal would make up a significant portion of the removed TOC currently unaccounted for. Large chain alcohols such as butanol and pentanol that were not completely removed in the unibeds could have also contributed to the TOC entering the immobilized enzyme beds. The immobilized enzyme beds effectively removed the targeted organics. Except for one instance, each organic specifically targeted for removal in the enzyme beds was removed below its detection limit. Additionally, based on the level of TOC removed, the enzyme beds are removing organics besides those specifically targeted.

The reactor beds have been developed from the proof-of-concept stage to successful CMIF tests of hardware that provides a relatively simple method for complete removal of urea and alcohols. Operational parameters for these materials were developed; pH, conductivity, temperature and other contaminants were tested in large and small column enzyme reactors. Urease enzyme beds currently function to completely remove 60 mg/L urea from solution for 45 L/cc, while alcohol oxidase-based catalysts convert 20 ppm(v/v) ethanol to acetic acid for 20 L/cc, at over 90% efficiency. Gamma irradiation and use of iodinated resin were identified as methods for maintaining microbial control of the biocatalyst beds for initial disinfection and supplying a downstream biocide residual, respectively. Further investigation is indicated in the use of gamma irradiation for sterilization of immobilized enzyme and multifiltration media. Immobilized enzyme technology, combined with multifiltration, provides the potential for a simple, energy-efficient means of producing high quality water aboard Space Station Freedom, particularly in early orbital configurations when power is limited.

TABLE 1

REACTIONS CATALYZED BY UMPQUA ALCOHOL OXIDASE CATALYST

| CONTAMINANT | PRODUCTS |
|---|---|
| METHANOL | FORMIC ACID |
| ETHANOL | ACETIC ACID |
| n-PROPANOL | PROPANOIC ACID |
| iso-PROPANOL | ACETONE |
| ALLYL ALCOHOL | ACRYLIC ACID |
| FORMALDEHYDE | FORMIC ACID |
| 2-CHLOROETHANOL | 2-CHLOROACETIC ACID |
| iso-PROPANOL | PROPANOIC ACID |
| ETHYL MERCAPTAN | UNIDENTIFIED |
| 2-MERCAPTOETHANOL | UNIDENTIFIED |
| n-BUTANOL | BUTANOIC ACID |
| 2-BUTYNE-1,4-DIOL | UNIDENTIFIED |

TABLE 2

POTABLE WATER RECLAMATION WITH MULTIFILTRATION SUPPLEMENTED BY IMMOBILIZED ENZYME BEDS

| | Waste Condensate | | | | | Unibed Outlet | | | | | Immobilized Enzyme Bed Outlet | | | | |
|---|---|---|---|---|---|---|---|---|---|---|---|---|---|---|---|
| Day | TOC | Etoh | Meoh | Isoh | Urea | TOC | Etoh | Meoh | Isoh | Urea | TOC | Etoh | Meoh | Isoh | Urea |
| 1 | 28.0 | 0.55 | 1.72 | 0.22 | 1.76 | | | | | | | | | | |
| 2 | 23.7 | 2.74 | 3.97 | 0.31 | 1.58 | 7.2 | 3.91 | 5.50 | 0.35 | 0.2 | 1.22 | <0.1 | 0.98 | | <0.1 |
| 3 | 19.6 | <0.1 | 0.59 | 0.27 | <0.1 | 4.92 | 2.66 | <0.41 | 0.29 | 0.12 | 0.86 | <0.1 | <0.41 | <0.2 | <0.1 |
| 4 | 28.7 | <0.1 | <0.41 | 0.26 | <0.1 | 5.61 | 2.76 | 0.7 | 0.27 | 0.13 | 0.72 | <0.1 | <0.41 | <0.2 | <0.1 |

TABLE 2-continued
POTABLE WATER RECLAMATION WITH MULTIFILTRATION SUPPLEMENTED BY IMMOBILIZED ENZYME BEDS

| Day | Waste Condensate | | | | | Unibed Outlet | | | | | Immobilized Enzyme Bed Outlet | | | | |
|---|---|---|---|---|---|---|---|---|---|---|---|---|---|---|---|
| | TOC | Etoh | Meoh | Isoh | Urea | TOC | Etoh | Meoh | Isoh | Urea | TOC | Etoh | Meoh | Isoh | Urea |
| 5 | 35.9 | <0.1 | <0.41 | 5.32 | <0.1 | 5.72 | 2.52 | 0.83 | 0.29 | 0.17 | 0.66 | <0.1 | <0.41 | <0.2 | <0.1 |
| 6 | 27.7 | 5.9 | <0.41 | 0.73 | <0.1 | 5.74 | 1.85 | <0.41 | 0.33 | 0.21 | 0.93 | <0.1 | <0.41 | <0.2 | <0.1 |
| 7 | 18.1 | <0.1 | <0.41 | 0.49 | <0.1 | 5.1 | 0.90 | 0.67 | 0.33 | 0.31 | <1.0 | <0.1 | <0.41 | <0.2 | <0.1 |
| 8 | 32.8 | <0.1 | <0.41 | 0.42 | <0.1 | | | | | | | | | | |
| 9 | 23.0 | 1.63 | <0.41 | <0.2 | <0.1 | 4.51 | 0.61 | 1.33 | 0.29 | 0.14 | <1.0 | <0.1 | <0.41 | <0.2 | <0.1 |
| 10 | | | | | | | | | | | 1.47 | <0.1 | <0.41 | <0.2 | <0.1 |
| 11 | 21.5 | 0.34 | 3.51 | 0.21 | <0.1 | 3.86 | 0.30 | <0.41 | 0.38 | 0.2 | 1.30 | <0.1 | <0.41 | <0.2 | <0.1 |

NOTE:
Meoh = methanol
Etoh = ethanol
Isa = isopropanol

I claim:

1. A method for removing low molecular weight contaminants from a contaminant-containing material, said low molecular weight contaminants including alcohol compounds and aldehyde compounds having up to three carbon atoms, which comprises:
   providing an alcohol oxidase enzyme-based catalyst system including co-immobilized transition metals comprising platinum and copper for catalytically oxidizing said contaminant-containing material;
   catalytically oxidizing said low molecular weight contaminants in the presence of said alcohol oxidase enzyme-based catalyst system to form organic acid compounds; and
   removing said organic acid compounds.

2. The method of claim 1, wherein said alcohol oxidase enzyme-based catalyst system includes an immobilized enzyme catalyst wherein the enzyme is bound to a derivatized support.

3. The method of claim 2, wherein the derivatized support comprises a silica-based material.

4. The method of claim 1, wherein said alcohol oxidase enzyme-based catalyst system is heterogeneous.

5. The method of claim 1, wherein the alcohol compounds and aldehyde compounds are oxidized according to the following chemical reactions:

$$RCH_2OH + O_2 \rightarrow RCHO + H_2O_2$$

$$RCHO + O_2 \rightarrow RCOOH + H_2O$$

6. The method of claim 1, wherein said organic acid compounds are removed by ion exchange.

7. The methods of claim 1, wherein said contaminant-containing material is catalytically oxidized using molecular oxygen.

8. The method of claim 7, wherein said molecular oxygen is employed as an oxidant in stoichiometric quantities.

9. The method of claim 7, wherein said molecular oxygen is accomplished using an oxygen saturator.

10. The methods of claim 9, wherein the oxygen saturator includes a hollow fiber, non-porous membrane bundle within an outer housing.

11. The method of claim 9, including the step of distributing dissolved oxygen throughout said contaminant-containing material, thereby avoiding two-phase flow that can occur if the molecular oxygen were simply injected into contaminant-containing material which can lead to gas bubble entrapment resulting in bed channeling or flow restriction.

12. A method for removing low molecular weight contaminants from a contaminant-containing material, said low molecular weight contaminants including alcohol compounds and aldehyde compounds having up to three carbon atoms, which comprises:
   providing an alcohol oxidase enzyme-based catalyst system including co-immobilized transition metals comprising platinum and copper for catalytically oxidizing said contaminant-containing material; and
   catalytically oxidizing said low molecular weight contaminants in the presence of said alcohol oxidase enzyme-based catalyst system.

13. The method of claim 12, wherein said alcohol oxidase enzyme-based catalyst system includes an immobilized enzyme catalyst wherein the enzyme is bound to a derivatized support.

14. The method of claim 13, wherein the derivatized support comprises a silica-based material.

15. The method of claim 12, wherein said alcohol oxidase enzyme-based catalyst system is heterogeneous.

16. The method of claim 12 wherein the alcohol compounds and aldehyde compounds are oxidized according to the following chemical reactions:

$$RCH_2OH + O_2 \rightarrow RCHO + H_2O_2$$

$$RCHO + O_2 \rightarrow RCOOH + H_2O$$

17. The methods of claim 12, wherein said contaminant-containing material is catalytically oxidized using molecular oxygen.

18. The method of claim 17, wherein said molecular oxygen is employed as an oxidant in stoichiometric quantities.

19. The method of claim 17, wherein said molecular oxygen is accomplished using an oxygen saturator.

20. The methods of claim 17, wherein the oxygen saturator includes a hollow fiber, non-porous membrane bundle within an outer housing.

21. The method of claim 19, including the step of distributing dissolved oxygen throughout said contaminant-containing material, thereby avoiding two-phase flow that can occur if the molecular oxygen were simply injected into contaminant-containing material which can lead to gas bubble entrapment resulting in bed channeling or flow restriction.

* * * * *

UNITED STATES PATENT AND TRADEMARK OFFICE
CERTIFICATE OF CORRECTION

PATENT NO. : 5,186,842
DATED : February 16, 1993
INVENTOR(S) : Clifford D. Jolly It is certified that error appears in the above-indentified patent and that said Letters Patent is hereby corrected as shown below:

Column 8  Line 55, change "17" to --19--.

Signed and Sealed this

Twenty-fourth Day of May, 1994

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,186,842
DATED : February 16, 1993
INVENTOR(S) : Clifford D. Jolly It is certified that error appears in the above-indentified patent and that said Letters Patent is hereby corrected as shown below:

Column 1   Line 4, add --This invention was made with Government support under Contract NAS8-38421 awarded by NASA. The Government has certain rights in this invention.--

Signed and Sealed this

Sixth Day of September, 1994

Attest:

BRUCE LEHMAN

*Attesting Officer*   *Commissioner of Patents and Trademarks*